US00PP26630P2

(12) United States Plant Patent
Kratzenberg

(10) Patent No.: US PP26,630 P2
(45) Date of Patent: Apr. 19, 2016

(54) ***GERANIUM* PLANT NAMED 'MISS HEIDI'**

(50) Latin Name: *Geranium×oxonianum*
Varietal Denomination: Miss Heidi

(71) Applicant: Ernst Benary Samenzucht GmbH, Hann. Münden (DE)

(72) Inventor: Sabine Kratzenberg, Hann. Münden (DE)

(73) Assignee: Ernst Benary Samenzucht GmbH, Hannoveroch Muenden (DE)

( * ) Notice: Subject to any disclaimer, the term of this patent is extended or adjusted under 35 U.S.C. 154(b) by 54 days.

(21) Appl. No.: 14/121,706

(22) Filed: Oct. 9, 2014

(51) Int. Cl.
*A01H 5/02* (2006.01)

(52) U.S. Cl.
USPC ..... Plt./324

(58) Field of Classification Search
USPC ..... Plt./324
CPC ..... A01H 5/0277
See application file for complete search history.

*Primary Examiner* — Kent L Bell
(74) *Attorney, Agent, or Firm* — Audrey Charles

(57) ABSTRACT

A new and distinct cultivar of *Geranium* plant named 'Miss Heidi', characterized by its medium pink-colored flowers having dark purple venation, dark green-colored foliage heavily marked with maroon-burgundy, and moderately vigorous, broadly mounded growth habit, is disclosed.

2 Drawing Sheets

Latin name of genus and species of plant claimed: *Geranium×oxonianum.*

Variety denomination: 'Miss Heidi'.

BACKGROUND OF THE INVENTION

The present invention relates to a new and distinct cultivar of *Geranium* plant botanically known as *Geranium×oxonianum* and hereinafter referred to by the cultivar name 'Miss Heidi'.

The new cultivar originated in a controlled breeding program in Hann. Münden, Germany during the summer of 2007. The objective of the breeding program was the development of *Geranium* cultivars having a long blooming time and a broadly mounded growth habit.

The new *Geranium* cultivar is the result of cross-pollination. The female (seed) parent of the new cultivar is 'Elworthy Misty', not patented, characterized by its medium pink-colored flowers with dark purple venation, medium green-colored foliage marked with maroon-burgundy, and moderately vigorous, semi-upright growth habit. The male (pollen) parent of the new cultivar is 'Königshof', not patented, characterized by its medium pink-colored flowers with dark purple venation, medium green-colored foliage, and moderately vigorous, semi-upright growth habit. The new cultivar was discovered and selected as a single flowering plant within the progeny of the above stated cross-pollination during the summer of 2008 in a controlled environment in Hann. Münden, Germany.

Asexual reproduction of the new cultivar by basal stem cuttings since the summer of 2008 in Hann. Münden, Germany and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Miss Heidi' as a new and distinct cultivar of *Geranium* plant:

1. Medium pink-colored flowers having dark purple venation;
2. Dark green-colored foliage heavily marked with maroon-burgundy; and
3. Moderately vigorous, broadly mounded growth habit.

Plants of the new cultivar differ from plants of the female parent primarily in having a darker foliage color and a more mounded growth habit. Plants of the new cultivar differ from plants of the male parent primarily in having foliage heavily marked with maroon-burgundy and a more mounded growth habit.

Of the many commercially available *Geranium* cultivars, the most similar in comparison to the new cultivar is 'Katherine Adele', not patented. However, in comparison, plants of the new cultivar differ from plants of 'Katherine Adele' in at least the following characteristics:

1. Plants of the new cultivar have a darker flower color than plants of 'Katherine Adele'; and
2. Plants of the new cultivar have more intense foliage markings than plants of 'Katherine Adele'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Miss Heidi'. The plants were grown in 1.5 gallon containers for approximately five months in a greenhouse in Elburn, Ill.

DETAILED BOTANICAL DESCRIPTION

Figure 1:
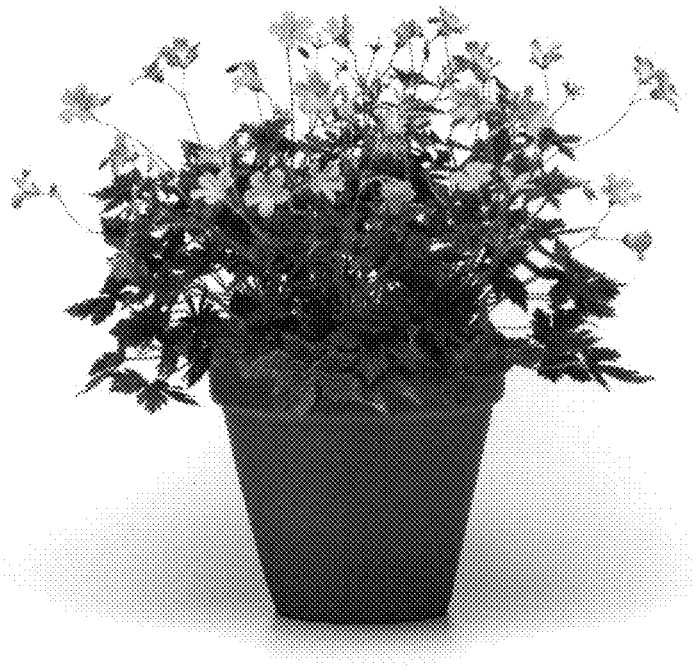
FIG. 1 illustrates a side view of the overall growth and flowering habit of 'Miss Heidi'.
Figure 2:
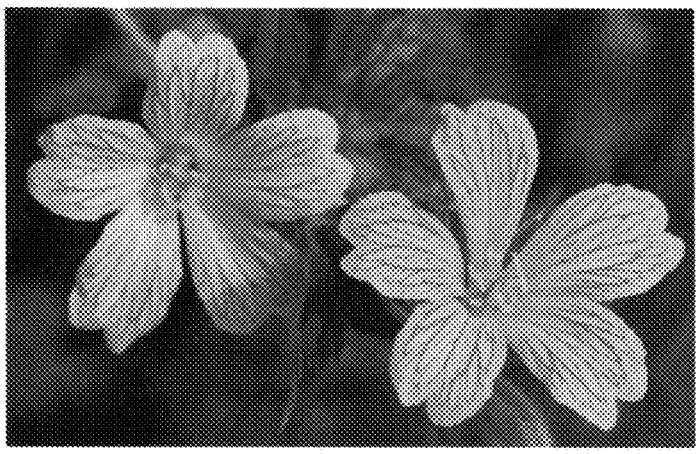
FIG. 2 illustrates a close-up view of fully-opened flowers of 'Miss Heidi'.
Figure 3:
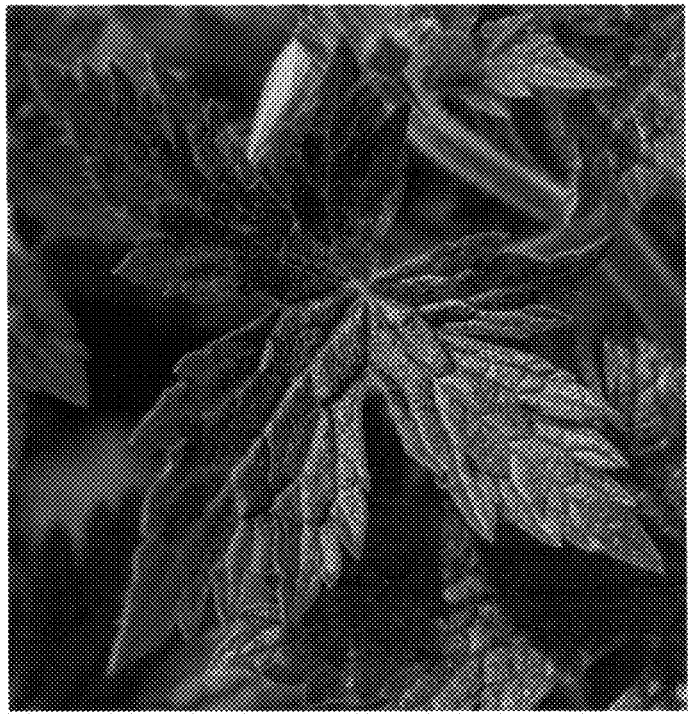
FIG. 3 illustrates a close-up view of a leaf of 'Miss Heidi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in September 2014 under natural light conditions in West Chicago, Ill.

The following descriptions and measurements describe plants produced from cuttings from stock plants and grown in a glass-covered greenhouse under conditions comparable to those used in commercial practice. The plants were grown utilizing a soilless growth medium in 1.5 gallon containers for approximately two months in a greenhouse and three months outdoors in Elburn, Ill. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Geranium×oxonianum* cultivar Miss Heidi.

Parentage:

*Female parent*.—'Elworthy Misty', not patented.

*Male parent*.—'Königshof', not patented.

Propagation:

*Type cutting*.—Basal stem.

*Time to initiate roots*.—Approximately 15 to 18 days.

*Time to produce a rooted cutting*.—Approximately 6 weeks.

*Root description*.—Fibrous, older roots fleshy.

*Rooting habit*.—Freely branching.

Plant description:

*Commercial crop time*.—Approximately 16 to 18 weeks from a rooted cutting to finish in a 15 cm pot.

*Growth habit and general appearance*.—Moderately vigorous, broadly mounded.

*Size*.—Height from soil level to top of plant plane: Approximately 32.0 cm. Width: Approximately 45.0 cm.

*Branching habit*.—Basal rosettes, flowering stems arise from the axils of the uppermost rosette leaves. Quantity of basal rosettes per plant: Approximately 9.

*Stems*.—Strength: Strong, slightly flexible. Length: Approximately 32.0 cm. Diameter: Approximately 5.0 mm. Length of central internode: Approximately 8.0 cm. Texture: Densely pubescent. Color of young and mature stems: 146B with 187A at nodes.

Foliage description:

*General description*.—Quantity of leaves per rosette: Approximately 10. Fragrance: None. Form: Simple. Arrangement on stem: Opposite.

*Leaves*.—Aspect: Leaf blade is primarily perpendicular to petiole. Shape: Orbicular. Margin: Parted, 5-lobed. Apex: Acute. Base: Hastate (not overlapping). Venation pattern: Palmate. Length: Approximately 11.0 cm. Width: Approximately 12.5 cm. Texture of upper surfaces: Moderately pubescent with appressed hairs. Texture of lower surfaces: Moderately pubescent with appressed hairs, densely pubescent on venation. Color of upper surface of young foliage: 137A with irregular markings of N187A and venation of 146A. Color of lower surface of young foliage: Closest to but greener than 191A with venation of 146D. Color of upper surface of mature foliage: N137A with irregular markings of N187A and venation of 146A. Color of lower surface of mature foliage: Closest to 191A with venation of 146D.

*Petiole*.—Length of rosette leaves: Approximately 29.0 cm. Diameter of rosette leaves: Approximately 3.0 mm. Length of stem leaves: Up to approximately 15.0 cm. Diameter of stem leaves: Approximately 2.0 mm. Texture: Densely pubescent. Color: 146B.

*Stipules*.—Shape: Narrowly Ovate. Margin: Entire, narrowly membrane-edged. Apex: Elongated acuminate. Base: Truncate. Length: Approximately 1.3 cm. Width: Approximately 4.0 mm. Texture of upper and lower surfaces: Densely pubescent with soft appressed hairs. Color of upper surface: 144C with base of 187A. Color of lower surface: 144A with base of 187A.

Flowering description:

*Flowering habit*.—'Miss Heidi' flowers heavily in the spring and sporadically throughout the summer.

*Lastingness of individual flower on the plant*.—Approximately 7 days, self-cleaning.

Flower description:

*General description*.—Type: Single, actinomorphic, arranged in axillary pairs. Flower aspect: Upward and outwardly facing. Quantity per plant: Approximately 13 with approximately 46 during spring flowering. Fragrance: None.

*Bud*.—Rate of opening: Generally takes 2 to 3 days for bud to progress from first color to fully open flower. Quantity showing color per plant: Approximately 2.

*Bud just before opening*.—Shape: Ovoid. Length: Approximately 1.2 cm. Diameter: Approximately 5.0 mm. Texture: Densely pubescent with a mixture of long and short hairs. Color: 137C with venation of 137B.

*Corolla*.—Shape: Funnel-shaped. Diameter: Approximately 3.1 cm. Depth: Approximately 1.3 cm.

*Petals*.—Quantity: Five in a single whorl, unfused. Shape: Obcordate. Appearance: Dull. Margin: Entire. Apex: Deeply emarginate. Base: Attenuate. Length: Approximately 1.9 cm. Width: Approximately 9.0 mm. Texture of upper surface: Glabrous, with densely pubescent base. Texture of lower surface: Glabrous. Color of upper surface when first and fully open: Closest to N74C with venation of N79C and base of NN155D. Color of lower surface when first and fully open: Closest to N74D with venation of N79C and base of NN155D.

*Calyx*.—Shape: Cupped. Length: Approximately 1.2 cm. Diameter: Approximately 1.5 cm.

*Sepals*.—Quantity per flower: 5 in a single whorl. Shape: Lanceolate. Margin: Entire, narrowly membrane-edged. Apex: Apiculate. Base: Truncate. Length: Approximately 1.2 cm. Width: Approximately 4.0 mm. Texture of upper (inner) surface: Glabrous. Texture of lower (outer) surface: Densely pubescent. Color of upper (inner) surface: 144B with venation of 137B, tip of 137B with 187A. Color of lower (outer) surface: 137C with venation of 137B, tip of 137B with 187A.

*Pedicel*.—Strength: Strong, flexible. Aspect: Nearly erect to an acute angle to peduncle. Length: Approximately 1.0 cm. Diameter: Approximately 1.0 mm. Texture: Densely pubescent. Color: 146B.

*Peduncle*.—Strength: Strong, moderately flexible. Aspect: Acute angle to stem. Length: Approximately 4.5 cm. Diameter: Approximately 2.0 mm. Texture: Densely pubescent. Color: 146B.

*Reproductive organs*.—Androecium: Stamen quantity: 10 per flower, arranged in 2 whorls. Stamen length: Approximately 9.0 mm. Filament color: Colorless, translucent. Anther shape: Bilobed, oblong, dorsifixed. Anther length: Approximately 1.5 mm. Anther color: 11D. Pollen amount: Sparse. Pollen color: 11C. Gynoecium: Pistil quantity: 1 per flower. Pistil texture: Densely pubescent. Pistil length: Approximately 1.0 cm. Stigma shape: 5-lobed. Stigma length: Approximately 4.0 mm. Stigma color: 185B. Style length: Approximately 2.0 mm. Style color: 144C. Ovary length: 4.0 mm. Ovary color: 137C.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'Miss Heidi', substantially as herein illustrated and described.

* * * * *